United States Patent [19]
Goodwin et al.

[11] Patent Number: 4,634,586
[45] Date of Patent: Jan. 6, 1987

[54] REAGENT AND METHOD FOR RADIOIMAGING LEUKOCYTES

[75] Inventors: David A. Goodwin, Atherton; Claude F. Meares, Davis, both of Calif.

[73] Assignee: The Board of Trustees of the Leland Stanford Junior University, Stanford, Calif.

[21] Appl. No.: 612,759

[22] Filed: May 21, 1984

[51] Int. Cl.$^4$ .................. A61K 43/00; A61K 49/00
[52] U.S. Cl. ........................ 424/1.1; 424/9; 424/85; 530/387; 435/35
[58] Field of Search ............... 424/1.1, 9, 85; 760/112 B

[56] References Cited

U.S. PATENT DOCUMENTS 4,454,106 6/1984 Gansow et al. ............ 424/1.1
4,497,791 2/1985 Gamble et al. ............ 424/1.1

OTHER PUBLICATIONS

Meares et al., Proc. Natl. Acad. Sci. USA, 73 (1976) 3803–3806.
Sundberg et al., J. Med. Chem., 17 (1974) 1304–1307.
Colas–Linhart et al., Chem. Abstracts, 98 (1983) #103851f.
Begent et al., The Lancet, Oct. 2, 1982, 739–742.
Bradwell et al., The Lancet, Jan. 29, 1983, p. 247.

Primary Examiner—Christine M. Nucker
Attorney, Agent, or Firm—Ciotti & Murashige

[57] ABSTRACT

Leukocytes are radioimmunoimaged by injecting patients with an immunoreactive nonleukocidal conjugate of an anti-leukocyte antibody and a gamma-emitting radioactive metal chelate, waiting for the conjugate to localize on the leukocytes, injecting the patient with an antibody to the conjugate to clear the blood of background nonlocalized conjugate, and visualizing the leukocytes by scintillation scanning.

16 Claims, No Drawings

REAGENT AND METHOD FOR RADIOIMAGING LEUKOCYTES

REFERENCE TO GOVERNMENT GRANT

This invention was made with Government support under grants nos 5 ROI CA 28343, CA 16861, and RCDA CA 00462 awarded by the National Institutes of Health. The Government has certain rights in this invention.

DESCRIPTION

1. Technical Field

This invention is in the field of radioimmunoimaging. More particularly it relates to reagents and methods for radioimaging leukocytes.

2. Background Art

Radioimmunoimaging refers to the use of radiolabeled antibodies or antibody fragments for in vivo detection of medical conditions. Its most common use is for imaging tumors. In that application a radiolabeled polyclonal or monoclonal antibody reagent that binds to a tumor-associated antigen is injected into the patient. The antibody is allowed to localize on the tumors and the tumors are imaged using radioimaging equipment such as a gamma camera, single-photon emission computed tomograph, or a positron emission computed tomograph.

Various radionuclides have been used in imaging applications including $^{67}Cu$, $^{67}Ga$, $^{72}As$, $^{89}Zr$, $^{97}Ru$, $^{99m}Tc$, $^{111}In$, and $^{123}I$. Antibodies have been labeled with these nuclides by various techniques depending upon the nuclide involved. In the case of radioactive metals, bifunctional chelating agents have been used to attach the nuclide to the antibody. These agents are molecules that contain both a chelating group that binds ions and a reactive functional group that is capable of reacting with protein side chains. The chelating group is generally a polyaminocarboxylic acid such as the phenyl or benzyl derivatives of ethylenediaminetetraacetic acid (EDTA) or diethylenetriaminepentaacetic acid (DTPA). The reactive functionality is usually a bromoacetyl group, a diazonium ion, an isothiocyanate or a carboxylic acid group. In the phenyl and benzyl derivatives of EDTA or DTPA the reactive functionality is substituted on the benzene ring.

Radioimmunoimaging has been used to evaluate the extent of tumor growth in lymph nodes. This radioimmunoimaging modality is called lymphoscintigraphy. Radiocolloids and radiolabeled antibodies have been used in lymphoscintigraphy. The radiolabeled antibodies for imaging metastases in the lymphatic system were to: (1) molecules, such as ferritin, that are sequestered in the lymph nodes or (2) tumor-associated antigens.

When radiolabeled antibodies are injected into circulation, radioimaging of sites of accumulation is hampered by the large amounts of circulating background activity that persists for several days. Previous investigators have reported using several procedures to compensate for or reduce background activity. Additional radiopharmaceuticals have been injected to outline the background areas so that they may be subtracted from the tumor images. Antigen binding fragments have been used rather than whole immunoglobulin because the fragments have accelerated rates of disappearance from the blood. Begent, R. H. J., et al, Lancet (1982) 2:739-742 describe using a liposomally entrapped second antibody to enhance clearance of radiolabeled antibodies to carcinoembryonic antigen from the blood.

DISCLOSURE OF THE INVENTION

There are several aspects to the present invention. One is a reagent for radioimmunoimaging leukocytes to visualize sites of leukocyte concentration and leukocyte radioimmunoimaging methods employing such reagents. Another is an improved method for clearing the blood of background activity. Kits for carrying out these procedures are another aspect.

The leukocyte radioimmunoimaging reagent comprises an immunoreactive nonleukocidal conjugate of an antibody to a leukocyte membrane determinant and a covalently attached radioactive metal chelate. A preferred reagent comprises a conjugate of a monoclonal antibody to human lymphocytes labeled with $^{111}In$ via a bifunctional benzyl derivative of EDTA or DTPA.

The leukocyte radioimmunoimaging method that employs this reagent involves injecting an effective amount of the reagent into a patient subcutaneously or intravenously. This method is used to visualize sites of leukocyte concentration such as lymph nodes, chronic inflammations, and absesses.

The blood clearance procedure is broadly applicable to reducing the amount a cell-localizing labeled serum protein from circulation to enhance imaging. It involves injecting a nonentrapped (free) antibody to the labeled serum protein that does not cross react with (i.e., does not bind to) endogenous components of the patient's blood. This is done after the labeled serum protein has had a chance to localize on the cells to be imaged.

MODES FOR CARRYING OUT THE INVENTION

The preposition "to" that is used to describe the immunoreactivity of an antibody denotes that the antibody binds specifically to the indicated antigen/antigenic determinant.

The term "nonleukocidal" that is used to describe the metal chelate-antibody conjugates means that the conjugate exhibits no or insignificant toxicity to leukocytes.

The term "leukocyte" is intended to include lymphocytes (B cells, T cells, and T cell subsets), granulocytes, and monocytes. Most uses of the invention will involve lymphocytes, i.e., B cells, T cells or T cell subsets, or granulocytes.

The term "patient" is intended to denote a mammalian individual. While most applications of the invention will involve human patients, it may be applied to farm, pet, or sport animals.

The term "monoclonal" is intended to denote a homogeneous immunoglobulin that has been produced by a single cell line, typically a single hybridoma or progeny thereof.

There are two antibody reagents that are involved in the invention: (1) the antibody-metal chelate conjugate that is used to tag the leukocytes to be imaged and (2) the anti-conjugate antibody that is used to clear circulating blood of radioactive conjugate that has not localized on the leukocytes. These antibodies may be monoclonal antibodies, affinity purified polyclonal antibodies, or antigen binding fragments of such monoclonal antibodies or affinity purified polyclonal antibodies.

The antibody partner of the conjugate is preferably a monoclonal antibody that recognizes and binds to a leukocyte membrane determinant. The determinant is not tumor specific. Such antibodies are available commercially or may be made by the somatic cell hybridization techniques described originally by Kohler, B. and Milstein, C., *Nature* (1975) 256:495-497 and reviewed at length in *Monoclonal Antibodies*, Kennett, T. J., et al, eds, Plenum (1980). Commercially available monoclonal antibodies to membrane determinants of leukocytes are represented by: the OKT anti-T monoclonal antibodies (available from Ortho Pharmaceutical Co.) which bind to normal T lymphocytes and T lymphocyte subsets; the monoclonal antibodies produced by the hybridomas having the ATCC accession numbers HB44, HB55, HB12, HB78 and HB2; G7E11, W8E7, NKP15, and G022 (Becton Dickinson); NEN9.4 (New England Nuclear); and FMC11 (Sera Labs). Available monoclonal antibodies to human leukocytes are typically of murine or rat origin and are IgGs or IgMs. The antibody partner of the conjugate is, however, not intended to be limited as regards species or Ig class or subclass.

Antibodies to leukocyte membrane determinants may be made by inoculating a host with leukocytes from the patient species. For instance antibodies for use in humans may be made by immunizing mice or other mammalian species with human leukocytes. Anti-human leukocyte serum may be collected from the host and affinity purified to provide polyclonal antibody for making the conjugate. Alternatively, splenocytes may be taken from the immunized host and fused with a suitable tumor cell line using the above mentioned somatic cell hybridization techniques to produce hybridomas that produce anti-leukocyte antibodies. These hybridomas may be isolated, subcloned and cultivated to produce monoclonal antibodies.

The conjugates are produced by reacting the anti-leukocyte antibody with the bifunctional chelating agent. Procedures for conjugating proteins and bifunctional chelating agents are reviewed by Wensel, T. G. and Meares, C. F. in *Radioimmunoimaging and Radioimmunotherapy* (1983) Elsevier, New York, pages 185-196. A preferred group of bifunctional chelating agents are those of the formula

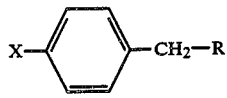

where X is a reactive functionality, such as bromoacetyl, diazonium ion, or isothiocyanate group, that reacts with amino acid side chains to covalently bind the chelating agent to the protein and R is EDTA or DTPA. There will typically be 1 to 4 chelating groups per antibody molecule. The chelating groups are bound to the antibody molecules at sites other than the antigen binding region, such as the Fc region, so that the immunoreactivity (i.e., the ability of the antibody to bind to the leukocyte membrane determinant) of the antibody is not affected adversely.

The conditions of the conjugation reaction will depend upon the chelating agent and the reactivity of the antibody. The concentration of the bifunctional chelating agent will usually be in the 0.1 to 2.0 mM range. When the conjugate is being prepared for subsequent labeling with $^{111}$In, the concentration of antibody in the reaction mixture will usually be in the range of about 10 to 30 mg/ml, typically about 20 mg/ml. A pH that minimizes the hydrolytic decomposition of the chelating agent and likelihood of antibody denaturation is preferred. The pH will usually be in the range of about 8 to 10. The mol ratio of chelating agent to antibody will usually be in the range of 1:1 to 20:1. Temperatures in the range of 25° C. to 37° C. are preferred. The reaction time will usually be between 1 and 2 hr. The resulting conjugate may be separated from unreacted chelating agent by gel filtration chromatography (Penefsky, H. S., *Meth in Enzymology* (1979) 56:527) or dialysis.

The radionuclide is usually added to the conjugate just before use. Preferred gamma-emitting nuclides are $^{99m}$Tc, $^{67}$Ga, $^{68}$Ga, and $^{111}$In. $^{111}$In is particularly preferred. Wensel, T. G. and Meares, C. F., supra, also describe the conditions for complexing the radionuclide with the conjugate. The metal complexing or chelation is carried out in aqueous solution. The pH will normally be 5 to 6.5. The metal is added as a metal salt, such as the citrate salt and the solution is normally citrate buffered. The temperature is not critical. Room temperatures may be used for convenience. The radiolabeled conjugate may be used without further purification.

The conjugate is formulated for injection in a unit dosage injectable form (solution, suspension, emulsion) in association with a pharmaceutically acceptable parenteral vehicle. Such vehicles are inherently nontoxic and nontherapeutic. Examples of such vehicles are water, saline, Ringer's solution and dextrose solution. The vehicle will preferably include a small amount e.g., in the range of 2-5% by volume of a carrier protein, such as human serum albumin, to stabilize the antibody and keep the conjugate from adhering to the surfaces of the vessels in which it is placed. The vehicle may also contain minor amounts of conventional additives such as substances that enhance isotonicity and stability, e.g., buffers and preservatives. The conjugate will typically be formulated in such vehicles at concentrations of about 0.5 mg/ml to 1 mg/ml.

The antibody that is used to clear background conjugate from circulation may be to any determinant site on the conjugate, provided it does not cross react with endogenous components of the patient's blood. When the antibody component of the conjugate is from a mammalian species that is different than the patient species, it is convenient to simply use an antibody that is directed against that species of antibody contained in the conjugate. For instance in the case of a conjugate that employs a murine antibody and is intended for use in radioimmunoimaging human leukocytes, an antibody to murine immunoglobulin may be used. If the antibody component of the conjugate is a human antibody and the conjugate is intended for use in radioimmunoimaging human leukocytes, it is not possible to use an antibody to human immunoglobulin. In this case the clearance antibody must be to a determinant site on a component of the conjugate other than the antibody. For instance, the antibody may be to the chelating group.

The clearance antibody is preferably a monoclonal antibody since monoclonal antibodies are homogeneous and typically may be used at much lower dosages than purified polyclonal sera to obtain equivalent results. Monoclonal antibodies and antisera to various species of mammalian immunoglobin are available commercially. Monoclonal antibodies to the chelating agent or other components of the conjugate may be made by the somatic cell hybridization procedures described above.

Clearance of the circulating conjugate occurs via the reticuloendothelial system and it has been found that conjugate that is complexed with an antibody of the IgM class is cleared more rapidly and completely from circulation than conjugate complexed with antibodies of other classes. The clearance antibody is not entrapped in liposomes or administered in any other form that would affect (delay or inhibit) its immunoreactivity. The free antibody is formulated for intravenous injection and the same parenteral vehicles as are used for formulating the conjugate may be used. The concentration of clearance antibody in the formulation will typically be in the range of 5 mg/ml to 10 mg/ml.

As indicated previously, the above described background clearance procedure may be applied to radioimmunoimaging modalities other than those described herein for imaging leukocytes. It may also be used in imaging procedures that use labels other than radionuclides, such as fluorescent or chemiluminescent labels.

Kits for radioimmunoimaging leukocytes according to the invention will typically lack a radioactive component due to the short half lives of the nuclides used in radioimaging and the dangers and difficulties involved in shipping radioactive materials. Thus the kits will contain only the components for making the antibody conjugate or the antibody-chelating agent conjugate ready for radiolabeling, leaving the user to supply the nuclide and complex it with conjugate. The components of the kits may vary accordingly. One form of kit may simply include the chelating agent with instructions on how to conjugate it to antibodies, complex the conjugate with the nuclide, formulate the complex and administer the complex. Such kits might optionally include chromatography materials (e.g., small column(s)) for purifying the conjugate, buffers that are used in preparing the conjugate/complex and dilution buffers optionally containing small amounts of chelating agent for formulating the complex for administration. Other forms of the kit may include the anti-leukocyte antibody-chelating agent conjugate, and the anti-conjugate antibody for clearing background activity together with instructions on how to form the radioactive metal complex and administer the complex and clearance antibody. The individual components of the kit will normally be contained in separate containers.

The particular protocol that is used to radioimage leukocytes according to this invention will depend, inter alia, upon the patient and the particular leukocytes to be imaged. For radioimaging sites of lymphocyte concentration such as lymph nodes, or chronic inflammations (sites of trauma, infection or disease), the radioactive conjugate is preferably injected at a subcutaneous site from which the conjugate will migrate rapidly to the expected site of accumulation. For instance if one wishes to visualize the axillary lymph nodes in a human patient the conjugate would be injected subcutaneously in the hands/arms. For radioimaging sites of granulocyte concentration, such as acute pyogenic absesses, the radiolabeled conjugate is preferably injected intravenously. The dose of conjugate administered will be sufficient to provide enough gamma emission to permit the target site to be visualized by scintillation scanning. It will normally be in the range of about 100 $\mu$g to 1 mg. The radioactive conjugate is then given time to accumulate at the site to be visualized. This will usually take approximately one day. The anti-conjugate antibody is then injected into the patient's circulation. The dose of anti-conjugate antibody will be sufficient to permit clearance of a substantial portion, preferably substantially all, of the free circulating conjugate. About 60 to 100 mg of the clearance antibody will usually be administered. The antibody is given time to bind to circulating conjugate and the resulting complex to be cleared by the liver. This will normally take about 10 to 15 min. The image is then produced using conventional imaging equipment such as that described under Background Art above.

The following examples further illustrate the invention. These examples are not intended to limit the invention in any manner.

Preparation of Conjugate

BALB/k mice were used as a model with BALB/c mice as control. Accordingly, a murine monoclonal anti-IA$^k$ antibody that recognizes a membrane antigen in B lymphocytes of BALB/k mice was used in making the conjugate. This antibody was obtained from Dr. H. O. McDevitt, Department of Immunology, Stanford University School of Medicine. This antibody was conjugated with 1-(p-bromoacetamidobenzyl)EDTA as described previously. The resulting conjugate had 1 to 3.3 chelating groups per antibody molecule. The conjugate was radiolabeled with 0.3–3.0 mCi $^{111}$In by adding 5–10 $\mu$l conjugate to 50 $\mu$l $^{111}$In citrate, pH 5.0. The specific activity of the $^{111}$In-labeled conjugate was approximately 300 Ci/mmol.

Radioimmunoimaging

The mice were injected IV with 0.2 ml of a normal saline solution of the conjugate (50 Ci $^{111}$In, 5 nmol protein) and subcutaneously in both hind footpads with 0.1 ml of the same solution. Other mice were injected similarly with $^{111}$In colloid (Goodwin, D. A., et al, *Radiology* (1970) 94:175–178) to permit comparison of the regional node uptake of the $^{111}$In anti-IA$^k$ and $^{111}$In colloid.

After IV injection, the BALB/k spleen, peripheral, and mesenteric nodes all had significantly higher concentration of radiolabeled anti-IA$^k$ conjugate than BALB/c ($p<0.01$); spleen 116%/gm (10.5% of dose), peripheral nodes 18%/gm (0.4% of dose); and mesenteric nodes 17.4%/gm (0.9% of dose). Following subcutaneous injections in both hind footpads, the regional popliteal and inguinal draining nodes contained 244%/gm (1.6% of dose), mesenteric nodes 17%/gm, cervical nodes 20%/gm, and spleen 95%/gm (8.3% of total dose) ($p<0.01$). The BALB/k to BALB/c ratios after subcutaneous injection were: regional nodes 11:1, mesenteric nodes 5.3:1, cervical nodes 4.4:1. After subcutaneous $^{111}$In colloid, there was no significant difference in organ or lymph node uptake between BALB/c and BALB/k mice. Absorption of subcutaneous $^{111}$In anti-IAk conjugate was more complete than $^{111}$In colloid ($p<0.001$): approximately 10% of the $^{111}$In anti-IA$^k$ conjugate remaining in the footpads at 24 hours compared to approximately 30% of the $^{111}$In colloid.

The above results demonstrate that $^{111}$In chelate tagged anti-lymphocyte antibodies rapidly accumulate in the lymphatic system and may be used to image that system. This procedure is distinct from analogous techniques to radioimmunoimage tumors in several respects. The antibodies are directed to a lymphocyte determinant that is not tumor-specific. Thus, they bind to normal (noncancerous) lymphocytes rather than tumors. Such determinants do not elute from the cells and there is, therefore, not a high amount of free (not associated with cells) determinant background. Also, the present conjugates are not toxic to lymphocytes and thus permit tagged cells to remain in circulation. Also, since the conjugates are not tumor-specific they permit visualization of noncancerous sites of lymphocyte concentration, such as inflammations caused by arthritic conditions, trauma or infection or abcesses.

While the above mode for tagging leukocytes involves administering the radioactive conjugate directly to the patient it will be appreciated that the leukocytes could be removed from the patient, treated in vitro with the conjugate and the tagged leukocytes injected back into the patient.

Clearance of Circulating Background

The feasibility of this procedure was shown in mice and dog models using $^{111}$In chelate conjugated human transferrin or human IgG as the radioimaging reagent and anti-human transferrin sera and anti-human IgG sera as the clearance reagents.

Materials and Methods

Human transferrin and IgG were alkylated with 1-(para-bromoacetamidobenzyl)EDTA. The dialyzed solutions (millimolar in protein concentration, approximately 1 chelate per molecule) were frozen for long-term storage at −80° C. in 20 μl aliquots. The proteins were radiolabeled with 0.3–3.0 mCi $^{111}$In by adding 5–20 μl protein solution to 50 μl $^{111}$In-citrate pH 5.0. The specific activity of the radiolabeled alkyl-proteins, $^{111}$In-transferrin, and $^{111}$In-IgG, was 10–450 Ci/mmol. Goat anti-human transferrin; titre 1:8, total protein 195 mg, and goat antihuman IgG; gamma chain specific, titre 1:16, total protein 109.4 mg, were purchased from Sigma Chemical Company. These lyophilized polyclonal antibodies were reconstituted in 2 ml deionized H$_2$O and used without further dilution. The mouse tumor model employed BALB/c mice with subcutaneously implanted KHJJ adenocarcinoma growing in the flank (Goodwin, et al, In: 18th Annual Clinical Conference Monograph 'Radiologic and other biophysical methods in tumor diagnosis' M. D. Anderson Hospital and Tumor Institute, Yearbook Medical Publishers, (1975) pp. 57–88). The experiments were done 2 weeks following implantation of the tumor. The mice were injected IV with 0.2 ml $^{111}$In-transferrin or $^{111}$In-IgG containing 10 μCi $^{111}$In and approximately 0.14–1.0 nmol protein. The animals were killed 18–24 hours later and samples of blood, tumor, and major organs were taken and assayed for radioactivity in a scintillation well counter.

In a group of six tumor-bearing mice, $^{111}$In-transferrin injection was followed in 2 hours by 0.2 ml (19.5 mg) anti-transferrin antibody IV in three of the six mice. In a second experiment, a similar IV injection of $^{111}$In-transferrin was given in a group of nine tumor-bearing mice, but the anti-transferrin antibody was not administered until 18 hours after the $^{111}$In-tranferrin injection in five of the mice. These were then killed 2 hours after the antibody injection.

A similar experiment was performed with $^{111}$In-human IgG of the same specific activity as the $^{111}$In-transferrin. Eleven tumor-bearing mice were injected IV with 10 μCi $^{111}$In-IgG followed by anti-IgG antibody injection 18 hours later in six of the eleven mice. These mice were killed at 20 hours and the organ distribution of radioactivity measured.

In order to determine the biological half-life of $^{111}$In-transferrin, three mice were injected IV with approximately 300 μCi each, and the whole body activity measured in a Victoreen dosimeter. This group consisted of two normal mice and one tumor-bearing mouse. The tumor mouse and one normal mouse had anti-transferrin antibody administered IV 24 hours after the injection of $^{111}$In-transferrin.

To determine the biological half-life in the circulation and organ distribution by scintillation imaging, a 15-kg mongrel dog was injected IV with 1 mCi $^{111}$In-transferrin and serial blood samples taken up to 30 hours. Anti-transferrin was administered IV on the day after $^{111}$In-transferrin injection, and the resultant changes in the distribution of activity monitored by serial scintillation images over the thorax and abdomen. The images were digitized, stored in a computer, and later analyzed by region of interest (ROI) analysis technique over the liver, heart, and lung. A dose-response experiment was done in which seven doses of anti-transferrin antibody, 19.5 mg each, were given IV to a dog at 15-minute intervals, 30 minutes following injection of $^{111}$In-transferrin, and the drop in blood activity in response to the antibody injections measured at the end of each 15-minute period.

Results

In the experiment with mice in which anti-transferrin antibody was injected 2 hours following $^{111}$In-alkyl-transferrin, the blood levels were reduced to 1/6 of the control value with a concomitant increase in liver concentration. However, the tumor concentrations reached only ⅓ of the control value and therefore, there was little increase in the tumor to blood ratio (2:1) due to the lower tumor concentration.

The injection of anti-transferrin antibody 18 hours after $^{111}$In-alkyl-transferrin reduced the blood level to approximately 1/48 of the control value; however, in this experiment there was no significant difference in the tumor concentration from the control value. As a result, the tumor to blood ratio increased from 1.4:1 to 78:1. Again, it was noted that the blood activity was mainly removed by the liver, with no deposition of immune complex in either bone marrow, spleen, or kidney.

Similar experiments were done using $^{111}$In-alkyl-IgG. A relatively high uptake of nonspecific human IgG was seen in the tumor at 20 hours; however, the tumor concentration was significantly less than the blood concentration. In this experiment, injection of anti-IgG antibody IV 2 hours before death reduced the blood concentrations to approximately 1/17 of the control value. There was no decrease in the tumor concentration caused by the antibody. The tumor to blood ratios increased from 0.7:1 to 17:1 and again the liver picked up the majority of the blood activity with none of the complex going to the spleen, bone marrow, or kidney. The slight drop in heart and lung concentrations were presumably secondary to decrease in the blood concentration.

The results of whole body counting in mice showed the biological half-life of the $^{111}$In-transferrin was approximately 4 days with no apparent effect of either tumor or antibody. There was a slower excretory phase of approximately 15% of the injected activity, becoming evident at 15–17 days.

The plasma disappearance data for $^{111}$In-transferrin in the dog study showed the biological half-life disappearance was 31.5 hours. The first injection of 98 mg anti-transferrin antibody at about 24 hours that had been reconstituted in deionized water the previous week produced only a partial response. The second injection at about 30.5 hours of 195 mg freshly reconstituted lyophilized anti-transferrin antibody produced a prompt drop in the blood $^{111}$In-transferrin levels. The drop in blood concentration was 90% complete in less than 15 minutes following the second antibody injection.

Modifications of the above described modes for carrying out the invention that are obvious to those of skill in radioimmunochemistry, radioimmunoimaging, and related fields are intended to be within the scope of the following claims.

We claim:

1. A leukocyte radioimmunoimaging reagent comprising an immunoreactive nonleukocidal conjugate of an antibody to a leukocyte membrane determinant and a bifunctional phenyl or benzyl derivatine of EDTA or DTPA chelated with a radioactive metal.

2. The reagent of claim 1 wherein the radioactive metal is $^{99m}$Tc, $^{67}$Ga, $^{68}$Ga or $^{111}$In and said derivative is of the formula

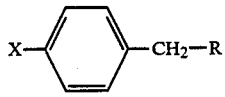

where X is a functionality that reacts with an amino acid side chain of the antibody to covalently bind the chelating agent to the antibody and R is EDTA.

3. The reagent of claim 1 wherein the antibody is a monoclonal antibody.

4. The reagent of claim 1 wherein the leukocyte is a lymphocyte or granulocyte.

5. The reagent of claim 1 wherein the leukocyte is a noncancerous human lymphocyte, the antibody is a monoclonal antibody to a nontumor-specific membrane determinant of the lymphocyte, the metal is $^{111}$In, and the bifunctional phenyl or benzyl derivative of EDTA or DTPA is 1-(p-bromoacetamidobenzyl) ethylenediaminetetraacetic acid.

6. A method for making leukocytes in a patient visible by radioimmunoimaging comprising injecting an effective amount of the reagent of claim 1 into the patient subcutaneously or intravenously.

7. A method of making leukocytes in a patient visible by radioimmunoimaging comprising injecting an effective amount of the reagent of claim 5 into the patient.

8. A method of making a site of expected lymphocyte concentration in a patient visible by radioimmunoimaging comprising injecting an effective amount of the reagent of claim 4 into the patient subcutaneously or intravenously at a location from which the reagent will migrate rapidly to the site.

9. The method of claim 8 wherein the site is a lymph node, an inflammation, or an absess.

10. A method of radioimaging leukocytes comprising injecting an effective amount of the reagent of claim 1 into the patient subcutaneously or intravenously, waiting until the conjugate localizes on the leukocytes of the patient, injecting into the patient's circulation an effective amount of antibody to the conjugate that does not cross react with endogenous components of the patient's blood, waiting for the reticuloendothial system to clear the patient's blood of complexes of the conjugate and the antibody to the conjugate, and visualizing the patient's leukocytes by scintillation scanning.

11. The method of claim 10 wherein the labeled serum protein is a leukocyte radioimmunoimaging reagent comprising an immunoreactive nonleukocidal conjugate of an antibody to a leukocyte membrane determinant and a radioactive metal chelate.

12. The method of claim 11 wherein the antibody to the conjugate is an IgM.

13. The method of claim 12 wherein the antibody to the conjugate is a monoclonal antibody.

14. The method of claim 11 wherein the antibody to the conjugate is to a determinant site on the antibody of the conjugate.

15. The method of claim 11 wherein the antibody to the conjugate is to a determinant site in the chelating agent of the conjugate.

16. A kit for use in radioimmunoimaging leukocytes in a patient comprising in:
(a) a first container containing conjugate of an antibody to a nontumor-specific membrane determinant of the leukocytes and a bifunctional benzyl or phenyl derivative of EDTA or DTPA; and
(b) a second container containing an antibody to the conjugate that does not cross react with endogenous components of the patient's blood.

* * * * *